US012661192B2

(12) United States Patent
Sage et al.

(10) Patent No.: US 12,661,192 B2
(45) Date of Patent: Jun. 23, 2026

(54) ROBOTIC SURGICAL SYSTEM WITH SINGLE MODE AND MULTIMODE OPTICAL COMMUNICATION

(71) Applicant: Covidien LP, Mansfield, MA (US)

(72) Inventors: Lawrence A. Sage, Killingworth, CT (US); Stephanie A. Mesick, Durham, CT (US)

(73) Assignee: Covidien LP, Mansfield, MA (US)

( * ) Notice: Subject to any disclaimer, the term of this patent is extended or adjusted under 35 U.S.C. 154(b) by 428 days.

(21) Appl. No.: 18/206,458

(22) Filed: Jun. 6, 2023

(65) Prior Publication Data

US 2024/0000522 A1     Jan. 4, 2024

Related U.S. Application Data

(60) Provisional application No. 63/356,675, filed on Jun. 29, 2022.

(51) Int. Cl.
| | |
|---|---|
| *A61B 34/30* | (2016.01) |
| *A61B 34/00* | (2016.01) |
| *A61B 34/20* | (2016.01) |
| *A61B 34/37* | (2016.01) |
| *A61B 90/00* | (2016.01) |

(52) U.S. Cl.
CPC ............. *A61B 34/30* (2016.02); *A61B 34/20* (2016.02); *A61B 34/37* (2016.02); *A61B 34/71* (2016.02); *A61B 90/361* (2016.02); *A61B 2034/2055* (2016.02); *A61B 2034/2059* (2016.02); *A61B 2034/301* (2016.02); *A61B 2090/3614* (2016.02); *A61B 2560/0437* (2013.01)

(58) Field of Classification Search
CPC .... G02B 6/4246; G02B 6/4416; A61B 34/30; A61B 34/37; A61B 90/361; A61B 34/20; A61B 34/35; A61B 2017/00477; A61B 34/25; A61B 34/71; A61B 90/37; A61B 2034/301; G16H 40/60
See application file for complete search history.

(56) References Cited

U.S. PATENT DOCUMENTS

| | | | |
|---|---|---|---|
| 6,132,368 A | 10/2000 | Cooper | |
| 6,206,903 B1 | 3/2001 | Ramans | |
| (Continued) | | | |

*Primary Examiner* — Michelle R Connelly
(74) *Attorney, Agent, or Firm* — Carter, DeLuca & Farrell, LLP

(57) ABSTRACT

A surgical robotic system includes a control tower having a first component configured to transmit and receive communication data, a first multimode fiber optic connection, a first single mode fiber optic connection and a first optical bulkhead connector coupled to the multimode fiber optic connection and the single mode fiber optic connection. The system also includes a surgeon console having a display configured to display video data, a second component configured to transmit and receive the communication data, a second multimode fiber optic connection, a second single mode fiber optic connection, a second optical bulkhead connector coupled to the second multimode fiber optic connection and the second single mode fiber optic connection. A main cable coupled to the first and second optical bulkhead connector, which interconnects the control tower and the surgeon console and is configured to transmit video data along with the communication data.

20 Claims, 5 Drawing Sheets

(56) References Cited

U.S. PATENT DOCUMENTS

| | | | |
|---|---|---|---|
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |
| 8,620,473 B2 | 12/2013 | Diolaiti et al. | |
| 8,624,537 B2 | 1/2014 | Nowlin et al. | |
| 8,634,957 B2 | 1/2014 | Toth et al. | |
| 8,638,056 B2 | 1/2014 | Goldberg et al. | |
| 8,638,057 B2 | 1/2014 | Goldberg et al. | |
| 8,644,988 B2 | 2/2014 | Prisco et al. | |
| 8,666,544 B2 | 3/2014 | Moll et al. | |
| 8,668,638 B2 | 3/2014 | Donhowe et al. | |
| 8,746,252 B2 | 6/2014 | McGrogan et al. | |
| 8,749,189 B2 | 6/2014 | Nowlin et al. | |
| 8,749,190 B2 | 6/2014 | Nowlin et al. | |
| 8,758,352 B2 | 6/2014 | Cooper et al. | |
| 8,761,930 B2 | 6/2014 | Nixon | |
| 8,768,516 B2 | 7/2014 | Diolaiti et al. | |
| 8,786,241 B2 | 7/2014 | Nowlin et al. | |
| 8,790,243 B2 | 7/2014 | Cooper et al. | |
| 8,808,164 B2 | 8/2014 | Hoffman et al. | |
| 8,816,628 B2 | 8/2014 | Nowlin et al. | |
| 8,821,480 B2 | 9/2014 | Burbank | |
| 8,823,308 B2 | 9/2014 | Nowlin et al. | |
| 8,827,989 B2 | 9/2014 | Niemeyer | |

(56)                    References Cited

U.S. PATENT DOCUMENTS

| | | | |
|---|---|---|---|
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Arkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Tkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,072,972 B2 | 9/2018 | Fusco et al. |
| 10,085,811 B2 | 10/2018 | Weir et al. |
| 10,092,165 B2 | 10/2018 | Power |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,838,816 B2 | 11/2020 | Arroyo et al. |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |

(56) References Cited

U.S. PATENT DOCUMENTS

| | | | |
|---|---|---|---|
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs, II et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Oh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 2010/0183053 A1* | 7/2010 | Tran | H04L 25/4904 |
| | | | 375/295 |
| 2017/0117971 A1* | 4/2017 | Sipes, Jr. | G02B 6/4292 |
| 2018/0228559 A1 | 8/2018 | Brierton et al. | |
| 2019/0206563 A1* | 7/2019 | Shelton, IV | G16H 50/20 |
| 2019/0216555 A1* | 7/2019 | DiMaio | A61B 90/50 |

* cited by examiner

ROBOTIC SURGICAL SYSTEM WITH SINGLE MODE AND MULTIMODE OPTICAL COMMUNICATION

CROSS-REFERENCE TO RELATED APPLICATIONS

The present application claims priority to and the benefit of U.S. Patent Provisional Application No. 63/356,675 filed on Jun. 29, 2022. The entire contents of the foregoing application are incorporated by reference herein.

BACKGROUND

Surgical robotic systems generally include a surgeon console controlling one or more surgical robotic arms, each including a surgical instrument having an end effector (e.g., forceps or grasping instrument) as well as a main control tower. The robotic systems operate using an endoscopic camera coupled to a camera control module. The systems may also include a main computer controlling all of the components of the system, i.e., the surgeon console, the robotic arms, the camera control module, etc. Due to the complexity of the robotic system, a large amount of data is transmitted between various components. Thus, there is a need for a cost-effective communication interface with high data throughput, e.g., 1 Gbps or above.

SUMMARY

The present disclosure provides a surgical robotic system including a control tower having a main computer and a camera control unit, which is coupled to an endoscopic camera. The system also includes a plurality of robotic arms each having an instrument coupled to an instrument drive unit configured to actuate the instrument. The system further includes a surgeon console having a pair of handle controllers configured to receive user input that is used to actuate the instrument. Each of the components of the system, i.e., control tower, surgeon console, robotic arms, etc. are interconnected by a plurality of cables. Due to the data demands of the system, the cable between the control tower and the surgeon console may be fiber optic cables that provide a higher bandwidth solution than conventional copper cables (e.g., Cat5e, Cat6 ethernet cables). The cables may include a plurality of optical fibers, each optical fiber configured to provide one or more communication channels.

The cables may be used to couple all of the components of the surgical robotic system, including connectivity between the control tower and the surgeon console. Upgraded cables support high bandwidth communications, e.g., 4K video, artificial intelligence augmentation, etc. as well as lower bandwidth communications, e.g., sensor data, logs, user inputs, etc. The system also includes optical transceivers configured to couple the cables to the components.

High bandwidth connections normally use single mode cables and transceivers, whereas low bandwidth connections use multimode cables and transceivers. Multimode transceivers are far less expensive and far more available that single mode transceivers. Thus, it would be desirable to use multimode transceivers with single mode transceivers. Where transmission distances are only a few meters, mixing of multimode transceivers with single mode devices has been shown to be possible without significant signal degradation. The proposed approach of using single mode transceivers in a multimode environment has not been adopted in any industry and the hybrid mode architecture (i.e., mixing of single mode and multimode transceivers and cables) of the present disclosure provides a unique solution for combining differing types of optical communications.

Transitioning from metal conductor cables to fiber optic cables for the surgical robotic system reduces the weight, diameter, cost, insertion/extraction force, connector size, and bend radius. These properties also increase the number of matings, crush strength, and reliability of the cable. Furthermore, incorporating fiber optic cables reduces the complexity and cost of upgrading the cables and enables support for higher bandwidth applications, such as stereoscopic vision.

According to one embodiment of the present disclosure, a surgical robotic system is disclosed. The surgical robotic system includes a camera configured to capture video data. The system also includes a control tower having a first component configured to transmit and receive communication data and a first multimode fiber optic connection. The control tower also includes a first single mode fiber optic connection and a first optical bulkhead connector coupled to the first multimode fiber optic connection and the first single mode fiber optic connection. The system also includes a surgeon console having a display configured to display video data, a second component configured to transmit and receive the communication data, a second multimode fiber optic connection, and a second single mode fiber optic connection. The surgeon console further includes a second optical bulkhead connector coupled to the second multimode fiber optic connection and the second single mode fiber optic connection. The system also includes a main cable coupled to the first optical bulkhead connector and the second optical bulkhead connector. The main cable interconnects the control tower and the surgeon console and is configured to transmit video data along with the communication data.

Implementations of the above embodiment may include one or more of the following features. According to one aspect of the above embodiment, the least one first multimode fiber optic connection and the second multimode fiber optic connection may be low bandwidth connections. The first single mode fiber optic connection and the second single mode fiber optic connection may be high bandwidth connections. The camera may be coupled to the first single mode fiber optic connection. The display may be coupled to the second single mode fiber optic connection. Each of the first multimode fiber optic connection and second multimode fiber optic connection may include at least one multimode fiber transceiver. Each of the first single mode fiber optic connection and the second single mode fiber optic connection may include at least one single mode fiber transceiver. Each of the at least one multimode fiber transceiver and the single mode fiber transceiver may be a small form factor pluggable transceiver. The first component and the second component may include at least one of a communication switch or a computer. The control tower further may include a camera control module coupled to the camera and configured to convert electrical signal from the camera into a single mode optical signal. The surgeon console further may include a video scaler module coupled to the display and configured to convert the single mode optical signal into an electrical signal for output on the display.

According to another embodiment of the present disclosure, a surgical robotic system is disclosed. The surgical robotic system includes a first computing device having a first multimode fiber optic connection, a first single mode fiber optic connection, and a first optical bulkhead connector coupled to the first multimode fiber optic connection and the single mode fiber optic connection. The system also includes a second computing device that may include: a second multimode fiber optic connection, a second single mode fiber optic connection, and a second optical bulkhead connector coupled to the second multimode fiber optic connection and the second single mode fiber optic connection. The system also includes a main cable coupled to the first optical bulkhead connector and the second optical bulkhead connector. The main cable interconnects the first computing device and the second computing device.

Implementations of the above embodiment may include one or more of the following features. According to one aspect of the above embodiment, the first multimode fiber optic connection and the second multimode fiber optic connection may be low bandwidth connections. The first single mode fiber optic connection and the second single mode fiber optic connection may be high bandwidth connections. The surgical robotic system may include a camera and a display. The camera may be coupled to the first single mode fiber optic connection. The display may be coupled the second single mode fiber optic connection. Each of the first multimode fiber optic connection and the second multimode fiber optic connection may include at least one multimode fiber transceiver. Each of the first single mode fiber optic connection and the second single mode fiber optic connection may include at least one single mode fiber transceiver. Each of the at least one multimode fiber transceiver and the single mode fiber transceiver may be a small form factor pluggable transceiver.

BRIEF DESCRIPTION OF THE DRAWINGS

Various embodiments of the present disclosure are described herein with reference to the drawings wherein.

DETAILED DESCRIPTION

Figure 1:
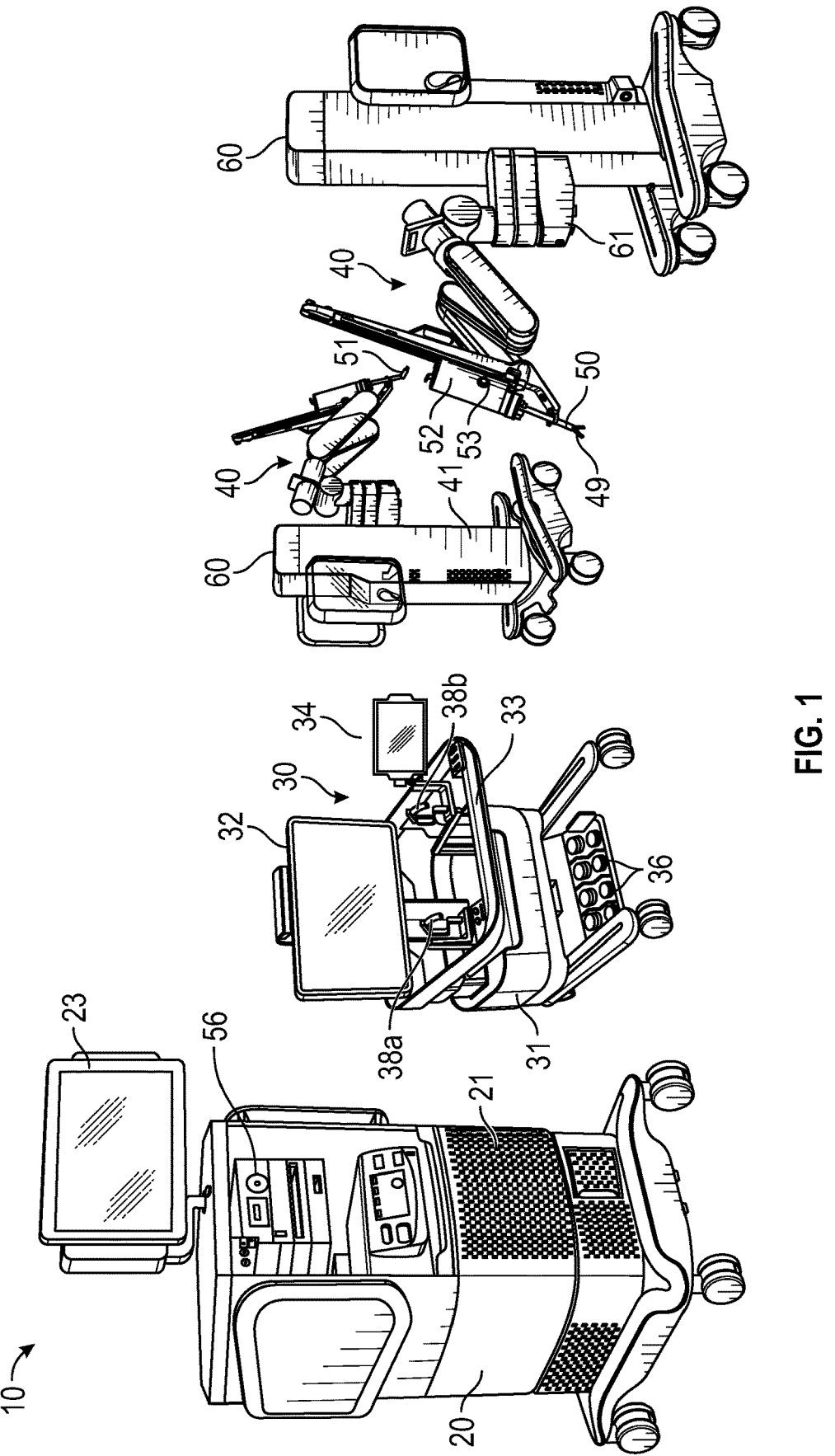
FIG. 1 is a schematic illustration of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more mobile carts having a surgical robotic arm coupled to a setup arm. The surgeon console receives user input through one or more interface devices, which are processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console and one or more movable carts 60. Each of the movable carts 60 includes a robotic arm 40 having a surgical instrument 50 removably coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include an endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 of the surgical instrument 50 disposed on the robotic arm 40, and a second display 34, which displays a user interface for controlling the surgical robotic system 10. The first display 32 and second display 34 may be touchscreens allowing for displaying various graphical user inputs.

The surgeon console 30 also includes a plurality of user interface devices, such as foot pedals 36 and a pair of handle controllers 38*a* and 38*b* which are used by a user to remotely control robotic arms 40. The surgeon console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38*a* and 38*b*. The foot pedals 36 may be used to enable and lock the hand controllers 38*a* and 38*b*, repositioning camera movement and electrosurgical activation/deactivation. In particular, the foot pedals 36 may be used to perform a clutching action on the hand controllers 38a and 38b. Clutching is initiated by pressing one of the foot pedals 36, which disconnects (i.e., prevents movement inputs) the hand controllers 38a and/or 38b from the robotic arm 40 and corresponding instrument 50 or camera 51 attached thereto. This allows the user to reposition the hand controllers 38a and 38b without moving the robotic arm(s) 40 and the instrument 50 and/or camera 51. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
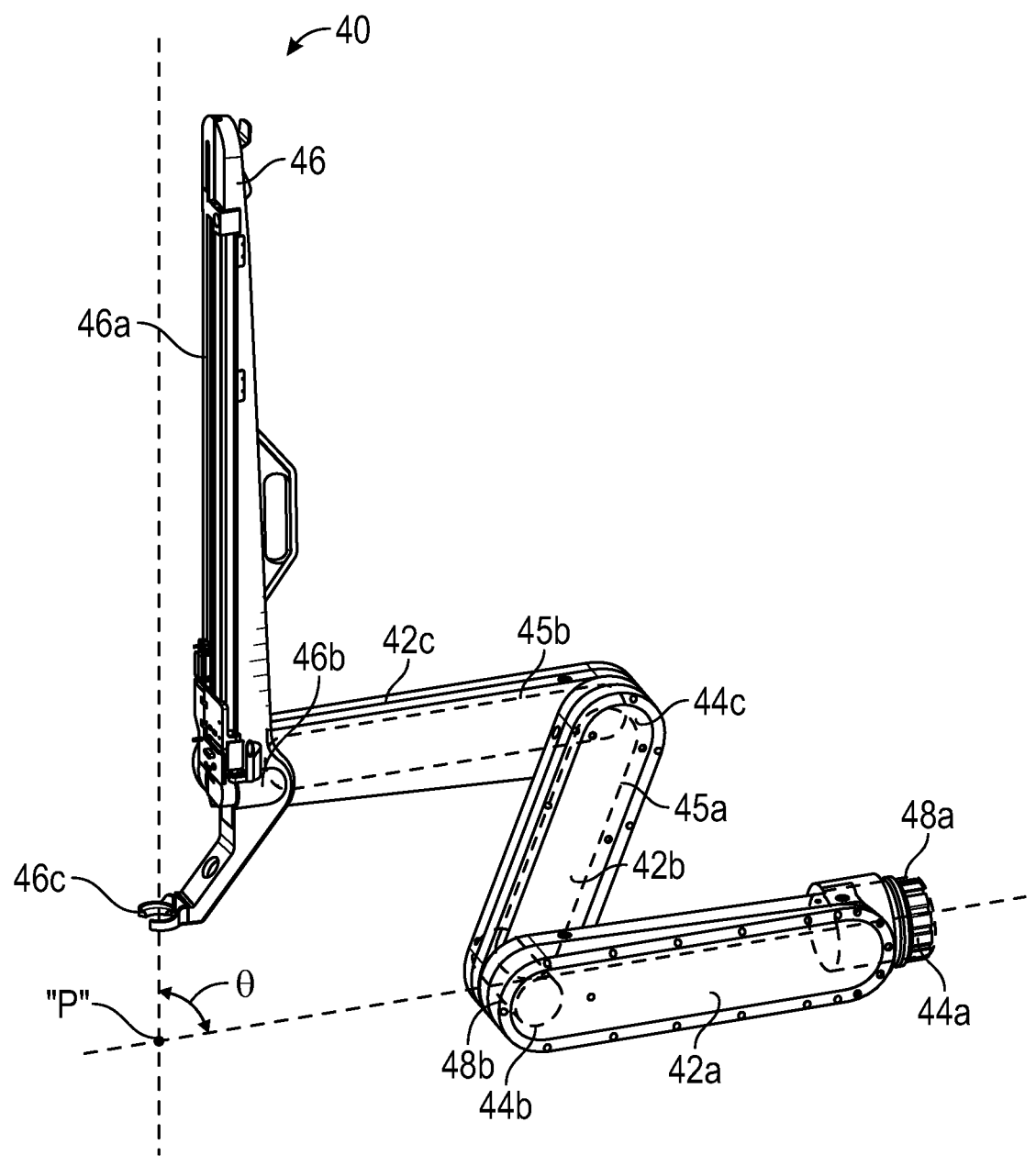
FIG. 2 is a perspective view of a surgical robotic arm of the surgical robotic system of FIG. 1 according to an embodiment of the present disclosure.
Figure 3:
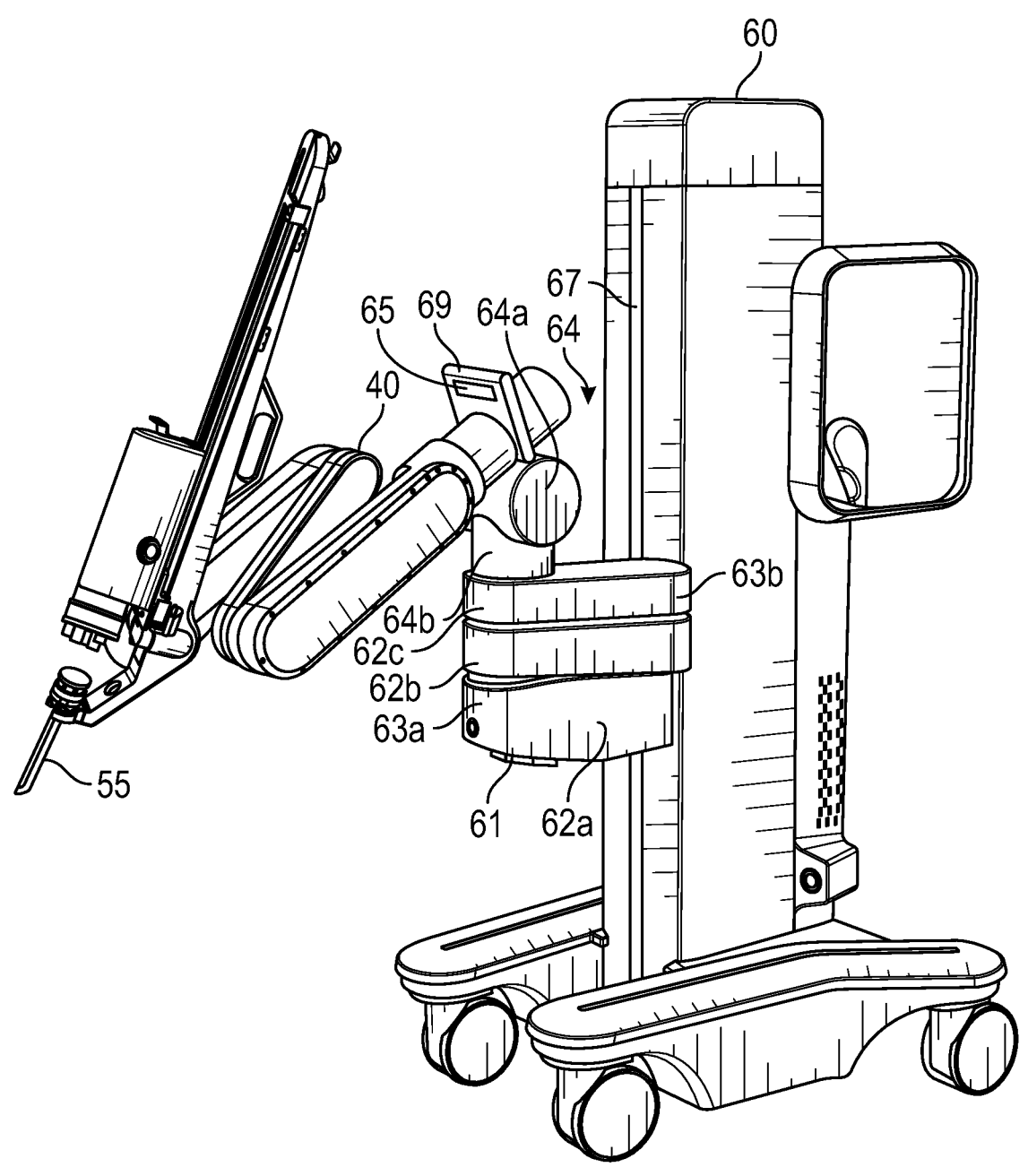
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. Other configurations of links and joints may be utilized as known by those skilled in the art. The joint 44a is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62a, 62b, 62c as well as the lift 67. In embodiments, the setup arm 61 may include any type and/or number of joints.

The third link 62c may include a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46b via the belt 45b. Joint 44c may include a transfer case coupling the belts 45a and 45b, such that the actuator 48b is configured to rotate each of the links 42b, 42c and a holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. In other words, the pivot point "P" is a remote center of motion (RCM) for the robotic arm 40. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the holder 46 defines a second longitudinal axis and is configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components an end effector 49 of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic access port 55 (FIG. 3) held by the holder 46. The holder 46 also includes a port latch 46c for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
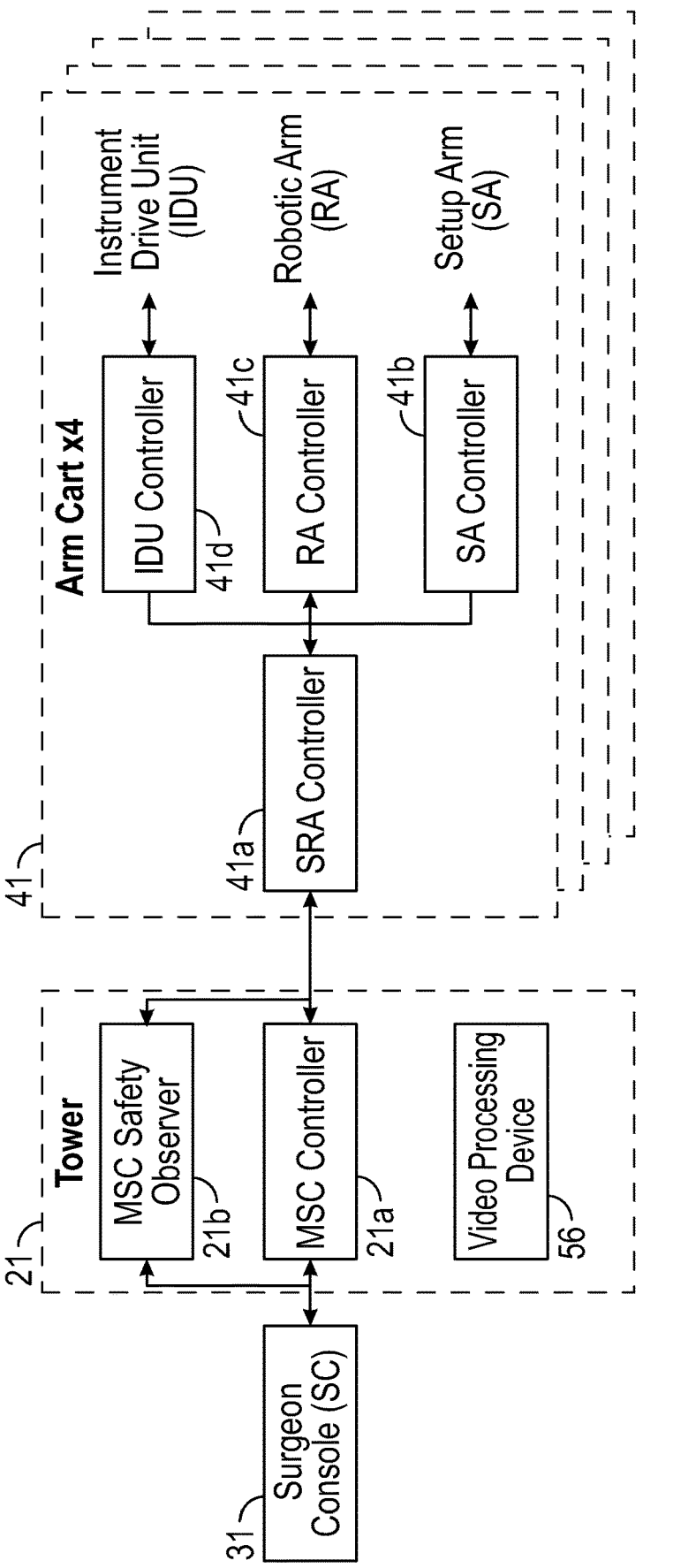
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the mobile cart 60, the robotic arm 40, and the IDU 52. The main cart controller 41a also communicates actual joint angles back to the controller 21a.

Each of joints 63a and 63b and the rotatable base 64 of the setup arm 61 are passive joints (i.e., no actuators are present therein) allowing for manual adjustment thereof by a user. The joints 63a and 63b and the rotatable base 64 include brakes that are disengaged by the user to configure the setup arm 61. The setup arm controller 41b monitors slippage of each of joints 63a and 63b and the rotatable base 64 of the setup arm 61, when brakes are engaged or can be freely moved by the operator when brakes are disengaged, but do not impact controls of other joints. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controllers 38a may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38a is then scaled by a scaling function executed by the controller 21a. In embodiments, the coordinate position may be scaled down and the orientation may be scaled up by the scaling function. In addition, the controller 21a may also execute a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
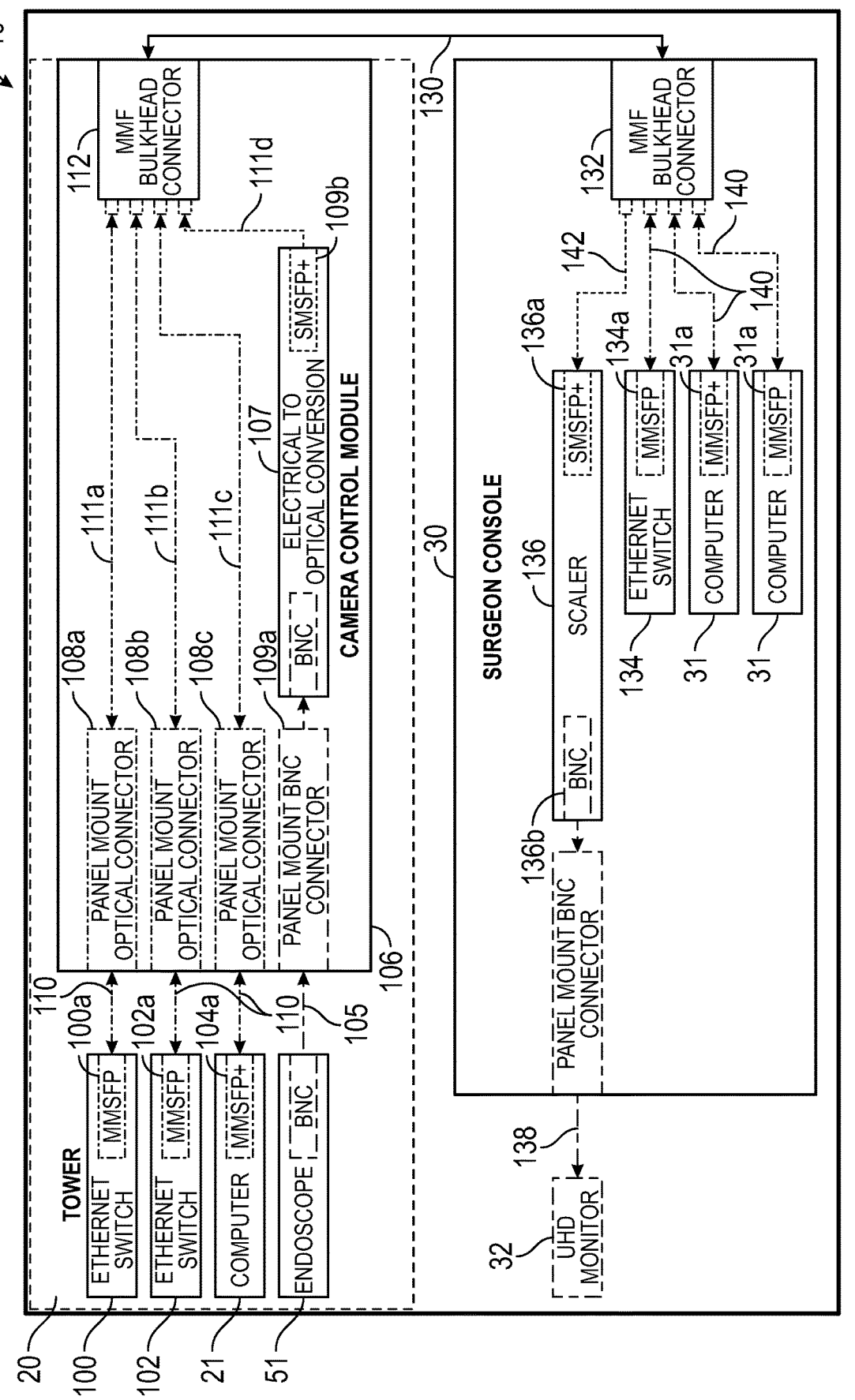
FIG. 5 is a schematic communications diagram of a surgeon console and a control tower according to an embodiment of the present disclosure.

FIG. 5 shows a communication architecture between a first computing device (e.g., control tower 20) and a second computing device (e.g., surgeon console 30) in the surgical robotic system 10. The control tower 20 includes one or more communication switches 100 and 102, which may be ethernet switches (e.g., 1 gigabit switches) configured to communicate over a network with other components of the system 10, such as the surgeon console 30 and the robotic arms 40 and may be used to transmit any suitable communication data between the control tower 20 and the surgeon console 30, such as user inputs, data logging, etc.

The control tower 20 also includes the computer 21, which receives data from the computer 31 of the surgeon console 30 about the current position and/or orientation of the handle controllers 38a and 38b and the state of the foot pedals 36 and other buttons. The computer 21 processes these input positions to determine desired drive commands for each joint of the robotic arm 40 and/or the IDU 52 and communicates these to the computer 41 of the robotic arm 40. The computer 21 also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The computer 21 performs validity checks on the data going into and out of the computer 21 and notifies a system fault handler if errors in the data transmission are detected to place the computer 21 and/or the surgical robotic system 10 into a safe state.

The control tower 20 also includes a camera control module 106, which may include or be coupled to the video processing device 56. The endoscopic camera 51 may utilize any video transmission protocol to transmit 4K video, such as SW PTE-2082. The endoscopic camera 51 may be coupled to the camera control module 106 using a video cable 105, which may be an SDI cable with BNC connectors having a bandwidth of about 12 GB/s or above.

The camera control module 106 includes an input connector 109*a* configured to couple to the video cable 105 and a conversion interface 107 that is configured to convert raw video signals from the camera 51 received over copper media (i.e., the video cable 105 and through the input connector 109*a*) to fiber media for transmission to the surgeon console 30. The conversion interface 107 also supports single mode (SM) fiber connectivity for optical transmission. In particular, the conversion interface 107 includes an output connector 109*b*, which may be an SM small form factor pluggable (SFP) transceiver connector that allows for high bandwidth transmission of video data. SFP transceiver connectors are network interface modules configured to convert communication signals between conductor and optical interfaces. SM interface provides a higher throughput, which makes it suitable for transmission of high bandwidth data, such as video data, and in particular high resolution video data (e.g., 4K video).

The camera control module 106 also acts as a communication interface for the components of the control tower 20, i.e., the switches 100 and 102, the computer 21, the endoscopic camera 51, etc. The camera control module 106 is also configured to convert communication data from the switches 100 and 102, the computer 21 to optical media allowing for combined transmission along with the video data.

The control module 106 may include a plurality of optical connectors 108*a-c* for connecting to the switches 100 and 102 and the computer 21. Each of the switches 100 and 102 and the computer 21 include optical connectors 100*a*, 102*a*, and 104*a*, respectively. The optical connectors 100*a*, 102*a*, 104*a* are configured to couple to the input optical connectors 108*a-c* using fiber optic cables 110. The optical connectors 100*a*, 102*a*, and 104*a* and the optical connectors 108*a-c* include integrated circuits for converting ethernet signal to optical signals and may be multimode (MM) fiber SFP transceiver connectors. While MM fiber connectors provide for a lower data throughput, they are less costly than SM counterparts. The fiber optic cables 110 may be MM fiber cables. MM fiber cables may include an optical fiber having a diameter of about 50 um and allow for transmission of multiple beams of light, i.e., multiple data streams. Multimode wavelengths may be either 850 nm or 1300 nm.

The camera control module 106 also includes an optical bulkhead connector 112, which may also be an MM fiber connector. The optical connectors 108*a-c* are coupled to the optical bulkhead connector 112 using MM fiber cables 111*a-c*. The output connector 109*b* of the conversion interface 107 is coupled to the optical bulkhead connector using an SM fiber cable 111*d*. SM fiber cables may include an optical fiber having a diameter of about 9 um and allow for transmission of a single beam of light, i.e., single data stream. Single mode wavelengths may be either 1310 nm or 1550 nm.

The optical bulkhead connector 112 is configured to connect to a main cable 130, which is an MM fiber cable, interconnecting the camera control module 106 (i.e., control tower 20) with the surgeon console. The main cable 130 may be optical multimode 3 (OM3) technology cable, which provides a cost-effective optical solution for short distance optical communication. While supports 1G ethernet directly, it does not support SDI-SM fiber-SDI. The present disclosure overcomes this shortcoming by SDI to SM fiber using the conversion interface 107 and combining SM with MM interfaces, counter to current industry practices and recommendation not to mix MM and SM media. This allows for transmission of high bandwidth video data (i.e., 4K endoscopic video) along with other communication data over MM fiber cable interconnecting the control tower 20 and the surgeon console 30.

The main cable 130 couples to an optical bulkhead connector 132 of the surgeon console 30. The optical bulkhead connector 132 acts like a splitter and is coupled to various components of the surgeon console 30 that are in communication with the control tower 20, i.e., one or more computers 31, a communication switch 134, and a video scaler 136. Each of the switch 134 and the computers 31 include optical connectors 134*a* and 31*a*, respectively. The optical connectors 134*a* and 31*a* include integrated MM fiber SFP transceiver connectors and are coupled to the optical bulkhead connector 132 via fiber optic cables 140, which may be MM fiber cables.

The video scaler 136 includes an optical input connector 136*a*, which may be an SM SFP transceiver connector that allows for high bandwidth transmission of video data from the endoscopic camera 51. The optical input connector 136*a* is coupled to the optical bulkhead connector 132 via fiber optic cable 142, which may be SM fiber cables. The video scaler 136 includes an output connector 136*b* configured to couple to the first display 32 of the surgeon console 30 for outputting real-time video feed of the endoscopic camera 51. The output connector 136*b* is coupled to the first display 32 using any suitable video cable 138, which may be an SDI cable with BNC connectors having a bandwidth of about 12 Gb/s or above.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
 a camera configured to capture video data;
 a control tower including:
  a first component configured to transmit and receive communication data;
  a first multimode fiber optic connection;
  a first single mode fiber optic connection; and
  a first optical bulkhead connector coupled to the first multimode fiber optic connection and the single mode fiber optic connection;
 a surgeon console including:
  a display configured to display video data;
  a second component configured to transmit and receive the communication data;
  a second multimode fiber optic connection;
  a second single mode fiber optic connection; and
  a second optical bulkhead connector coupled to the second multimode fiber optic connection and the second single mode fiber optic connection; and
 a main cable coupled to the first optical bulkhead connector and the second optical bulkhead connector, the main cable interconnecting the control tower and the surgeon console and configured to transmit video data along with the communication data.

2. The surgical robotic system according to claim 1, wherein the first multimode fiber optic connection and the second multimode fiber optic connection are low bandwidth connections.

3. The surgical robotic system according to claim 1, wherein the first single mode fiber optic connection and the second single mode fiber optic connection are high bandwidth connections.

4. The surgical robotic system according to claim 3, wherein the camera is coupled to the first single mode fiber optic connection.

5. The surgical robotic system according to claim 3, wherein the display is coupled to the second single mode fiber optic connection.

6. The surgical robotic system according to claim 1, wherein each of the first multimode fiber optic connection and the second multimode fiber optic connection includes at least one multimode fiber transceiver.

7. The surgical robotic system according to claim 6, wherein each of the first single mode fiber optic connection and the second single mode fiber optic connection includes at least one single mode fiber transceiver.

8. The surgical robotic system according to claim 7, wherein each of the at least one multimode fiber transceiver and the single mode fiber transceiver is a small form factor pluggable transceiver.

9. The surgical robotic system according to claim 1, wherein the first component and the second component include at least one of a communication switch or a computer.

10. The surgical robotic system according to claim 1, wherein the control tower further includes a camera control module coupled to the camera and configured to convert electrical signal from the camera into a single mode optical signal.

11. The surgical robotic system according to claim 1, wherein the surgeon console further includes a video scaler module coupled to the display and configured to convert the single mode optical signal into an electrical signal for output on the display.

12. A surgical robotic system comprising:

a first computing device including:

a first multimode fiber optic connection;

a first single mode fiber optic connection; and a first optical bulkhead connector coupled to the first multimode fiber optic connection and the single mode fiber optic connection;

a second computing device including:

a second multimode fiber optic connection;

a second single mode fiber optic connection; and a second optical bulkhead connector coupled to the second multimode fiber optic connection and the second single mode fiber optic connection; and a main cable coupled to the first optical bulkhead connector and the second optical bulkhead connector, the main cable interconnects the first computing device and configured the second computing device.

13. The surgical robotic system according to claim 12, wherein the first multimode fiber optic connection and the second multimode fiber optic connection are low bandwidth connections.

14. The surgical robotic system according to claim 12, wherein the first single mode fiber optic connection and the second single mode fiber optic connection are high bandwidth connections.

15. The surgical robotic system according to claim 12, further comprising a camera and a display.

16. The surgical robotic system according to claim 15, wherein the camera is coupled to the first single mode fiber optic connection.

17. The surgical robotic system according to claim 15, wherein the display is coupled the second single mode fiber optic connection.

18. The surgical robotic system according to claim 12, wherein each of the first multimode fiber optic connection and the second multimode fiber optic connection includes at least one multimode fiber transceiver.

19. The surgical robotic system according to claim 18, wherein each of the first single mode fiber optic connection and the second single mode fiber optic connection includes at least one single mode fiber transceiver.

20. The surgical robotic system according to claim 19, wherein each of the at least one multimode fiber transceiver and the at least one single mode fiber transceiver is a small form factor pluggable transceiver.

* * * * *